United States Patent [19]

Cherpeck

[11] Patent Number: 5,441,544
[45] Date of Patent: Aug. 15, 1995

[54] FUEL COMPOSITIONS CONTAINING SUBSTITUTED POLY(OXYALKYLENE) AROMATIC ETHERS

[75] Inventor: Richard E. Cherpeck, Cotati, Calif.

[73] Assignee: Chevron Chemical Company, San Ramon, Calif.

[21] Appl. No.: 173,817

[22] Filed: Dec. 23, 1993

[51] Int. Cl.⁶ .................................................. C10L 1/18
[52] U.S. Cl. ........................................ 44/384; 44/388; 44/400; 44/410; 44/418; 44/435; 568/32; 568/45; 568/62; 568/75; 564/170; 558/423
[58] Field of Search ............... 44/388, 435, 400, 410, 44/418, 384; 568/32, 45, 62, 75; 564/170; 558/423

[56] References Cited

U.S. PATENT DOCUMENTS

| | | | |
|---|---|---|---|
| 3,149,933 | 9/1964 | Ley et al. | 44/75 |
| 3,434,814 | 3/1969 | Dubeck et al. | 44/69 |
| 3,615,295 | 10/1971 | Manary, Jr. | 44/443 |
| 3,849,085 | 11/1974 | Kreuz et al. | 44/78 |
| 3,920,414 | 11/1975 | Steere et al. | 44/435 |
| 4,134,846 | 1/1979 | Machleder et al. | 252/51.5 A |
| 4,191,537 | 3/1980 | Lewis et al. | 44/71 |
| 4,320,020 | 3/1982 | Lange | 252/51.5 R |
| 4,320,021 | 3/1982 | Lange | 252/51.5 R |
| 4,347,148 | 8/1982 | Davis | 252/51.5 R |
| 4,386,939 | 6/1983 | Lange | 44/63 |
| 4,533,690 | 8/1985 | Rosequist | 524/161 |
| 4,609,474 | 9/1986 | Reisberg et al. | 252/8.55 D |
| 5,081,295 | 1/1992 | Reardan et al. | 564/163 |
| 5,090,914 | 2/1992 | Reardan et al. | 435/188 |

FOREIGN PATENT DOCUMENTS

0331086 9/1989 European Pat. Off. .
8912158 12/1989 WIPO .

*Primary Examiner*—Jacqueline V. Howard
*Attorney, Agent, or Firm*—C. J. Caroli

[57] ABSTRACT

A fuel additive having the formula:

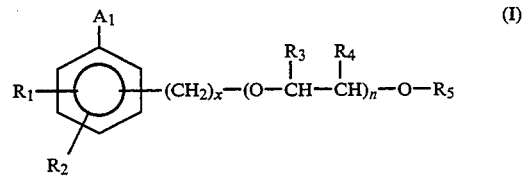

(I)

where $A_1$ is a thioether, a sulfoxide, a sulfone, a sulfonic acid, a sulfonamide, a nitrile, a carboxylic acid or ester, or a carboxamide; $R_1$ and $R_2$ are independently hydrogen, hydroxy, lower alkyl, or lower alkoxy; $R_3$ and $R_4$ are independently hydrogen or lower alkyl and each $R_3$ and $R_4$ is independently selected in each $-O-CHR_3-CHR_4-$ unit; $R_5$ is hydrogen, alkyl having 1 to 100 carbon atoms, phenyl, aralkyl having 7 to 100 carbon atoms or alkaryl having 7 to 100 carbon atoms, or an acyl group of the formula:

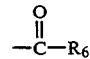

where $R_6$ is alkyl having 1 to 30 carbon atoms, phenyl, aralkyl having 7 to 36 carbon atoms or alkaryl having 7 to 36 carbon atoms; n is an integer from 5 to 100; and x is an integer from 0 to 10.

41 Claims, No Drawings

FUEL COMPOSITIONS CONTAINING SUBSTITUTED POLY(OXYALKYLENE) AROMATIC ETHERS

BACKGROUND OF THE INVENTION

1. Field of the Invention

This invention relates to poly(oxyalkylene) aromatic ethers and to fuel compositions containing poly(oxyalkylene) aromatic ethers. More particularly, this invention relates to poly(oxyalkylene) aromatic ethers which are substituted on the aromatic moiety and to the use of such compounds in fuel compositions to prevent and control engine deposits.

2. Description of the Related Art

It is well known that automobile engines tend to form deposits on the surface of engine components, such as carburetor ports, throttle bodies, fuel injectors, intake ports and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

For example, aliphatic hydrocarbon-substituted phenols are known to reduce engine deposits when used in fuel compositions. U.S. Pat. No. 3,849,085, issued Nov. 19, 1974 to Kreuz et al., discloses a motor fuel composition comprising a mixture of hydrocarbons in the gasoline boiling range containing about 0.01 to 0.25 volume percent of a high molecular weight aliphatic hydrocarbon-substituted phenol in which the aliphatic hydrocarbon radical has an average molecular weight in the range of about 500 to 3,500. This patent teaches that gasoline compositions containing minor amounts of an aliphatic hydrocarbon-substituted phenol not only prevent or inhibit the formation of intake valve and port deposits in a gasoline engine, but also enhance the performance of the fuel composition in engines designed to operate at higher operating temperatures with a minimum of decomposition and deposit formation in the manifold of the engine.

Similarly, U.S. Pat. No. 4,134,846, issued Jan. 16, 1979 to Machleder et al., discloses a fuel additive composition comprising a mixture of (1) the reaction product of an aliphatic hydrocarbon-substituted phenol, epichlorohydrin and a primary or secondary mono- or polyamine, and (2) a polyalkylene phenol. This patent teaches that such compositions show excellent carburetor, induction system and combustion chamber detergency and, in addition, provide effective rust inhibition when used in hydrocarbon fuels at low concentrations.

Amino phenols are also known to function as detergents/dispersants, antioxidants and anti-corrosion agents when used in fuel compositions. U.S. Pat. No. 4,320,021, issued Mar. 16, 1982 to R. M. Lange, for example, discloses amino phenols having at least one substantially saturated hydrocarbon-based substituent of at least 30 carbon atoms. The amino phenols of this patent are taught to impart useful and desirable properties to oil-based lubricants and normally liquid fuels.

Similar amino phenols are disclosed in related U.S. Pat. No. 4,320,020, issued Mar. 16, 1982 to R. M. Lange.

Similarly, U.S. Pat. No. 3,149,933, issued Sep. 22, 1964 to K. Ley et al., discloses hydrocarbon-substituted amino phenols as stabilizers for liquid fuels.

U.S. Pat. No. 4,386,939, issued Jun. 7, 1983 to R. M. Lange, discloses nitrogen-containing compositions prepared by reacting an amino phenol with at least one 3- or 4-membered ring heterocyclic compound in which the hetero atom is a single oxygen, sulfur or nitrogen atom, such as ethylene oxide. The nitrogen-containing compositions of this patent are taught to be useful as additives for lubricants and fuels.

Nitro phenols have also been employed as fuel additives. For example, U.S. Pat. No. 4,347,148, issued Aug. 31, 1982 to K. E. Davis, discloses nitro phenols containing at least one aliphatic substituent having at least about 40 carbon atoms. The nitro phenols of this patent are taught to be useful as detergents, dispersants, antioxidants and demulsifiers for lubricating oil and fuel compositions.

Similarly, U.S. Pat. No. 3,434,814, issued Mar. 25, 1969 to M. Dubeck et al., discloses a liquid hydrocarbon fuel composition containing a major quantity of a liquid hydrocarbon of the gasoline boiling range and a minor amount sufficient to reduce exhaust emissions and engine deposits of an aromatic nitro compound having an alkyl, aryl, aralkyl, alkanoyloxy, alkoxy, hydroxy or halogen substituent.

Fuel additives containing a poly(oxyalkylene) moiety are also known in the art. For example, U.S. Pat. No. 4,191,537, issued Mar. 4, 1980 to R. A. Lewis et al., discloses a fuel composition comprising a major portion of hydrocarbons boiling in the gasoline range and from 30 to 2000 ppm of a hydrocarbyl poly(oxyalkylene) aminocarbamate having a molecular weight from about 600 to 10,000, and at least one basic nitrogen atom. The hydrocarbyl poly(oxyalkylene) moiety is composed of oxyalkylene units selected from 2 to 5 carbon oxyalkylene units. These fuel compositions are taught to maintain the cleanliness of intake systems without contributing to combustion chamber deposits.

Aromatic compounds containing a poly(oxyalkylene) moiety are also known in the art. For example, the above-mentioned U.S. Pat. No. 4,191,537, discloses alkylphenyl poly(oxyalkylene) polymers which are useful as intermediates in the preparation of alkylphenyl poly(oxyalkylene) aminocarbamates.

Similarly, U.S. Pat. No. 5,090,914, issued Feb. 25, 1992 to D. T. Reardan et al., discloses poly(oxyalkylene) aromatic compounds having an amino or hydrazinocarbonyl substituent on the aromatic moiety and an ester, amide, carbamate, urea or ether linking group between the aromatic moiety and the poly(oxyalkylene) moiety. These compounds are taught to be useful for modifying macromolecular species such as proteins and enzymes. U.S. Pat. Nos. 5,081,295; 5,103,039; and 5,157,099; all issued to D. T. Reardan et al., disclose similar poly(oxyalkylene) aromatic compounds.

In addition, U.S. Pat. No. 4,231,759, issued Nov. 4, 1980 to Udelhofen et al., discloses a fuel additive composition comprising the Mannich condensation product of (1) a high molecular weight alkyl-substituted hydroxyaromatic compound wherein the alkyl group has a number average molecular weight of about 600 to about 3,000, (2) an amine, and (3) an aldehyde. This patent teaches that such Mannich condensation products provide carburetor cleanliness when employed alone, and intake valve cleanliness when employed in combination with a hydrocarbon carrier fluid.

U.S. Pat. No. 4,859,210, issued Aug. 22, 1989 to Franz et al., discloses fuel compositions containing (1) one or more polybutyl or polyisobutyl alcohols wherein the polybutyl or polyisobutyl group has a number average molecular weight of 324 to 3,000, or (2) a poly(alkoxylate) of the polybutyl or polyisobutyl alcohol, or (3) a carboxylate ester of the polybutyl or polyisobutyl alcohol. This patent further teaches that when the fuel composition contains an ester of a polybutyl or polyisobutyl alcohol, the ester-forming acid group may be derived from saturated or unsaturated, aliphatic or aromatic, acyclic or cyclic mono- or polycarboxylic acids.

U.S. Pat. No. 3,285,855, issued Nov. 15, 1966 to Dexter et al., discloses alkyl esters of dialkyl hydroxybenzoic and hydroxyphenylalkanoic acids wherein the ester moiety contains from 6 to 30 carbon atoms. This patent teaches that such esters are useful for stabilizing polypropylene and other organic material normally subject to oxidative deterioration. Similar alkyl esters containing hindered dialkyl hydroxyphenyl groups are disclosed in U.S. Pat. No. 5,196,565, which issued Mar. 23, 1993 to Ross.

U.S. Pat. No. 5,196,142, issued Mar. 23, 1993 to Mollet et al., discloses alkyl esters of hydroxyphenyl carboxylic acids wherein the ester moiety may contain up to 23 carbon atoms. This patent teaches that such compounds are useful as antioxidants for stabilizing emulsion-polymerized polymers.

It has now been discovered that certain poly(oxyalkylene) aromatic ethers which are substituted on the aromatic moiety are surprisingly useful for reducing engine deposits, especially intake valve deposits, when employed as fuel additives in fuel compositions.

SUMMARY OF THE INVENTION

The present invention provides novel substituted poly(oxyalkylene) aromatic ethers which are useful as fuel additives for the prevention and control of engine deposits, particularly intake valve deposits.

The substituted poly(oxyalkylene) aromatic ethers of the present invention have the formula:

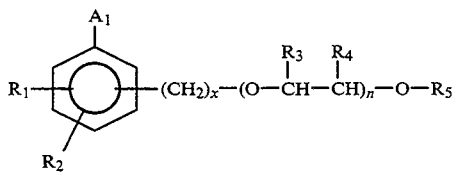

(I)

wherein $A_1$ is selected from the group consisting of $SR^I$, $SOR^{II}$, $SO_2R^{III}$, wherein $R^I$, $R^{II}$ and $R^{III}$ are independently lower alkyl of 1 to 6 carbon atoms; $SO_3H$; $SO_2NR^{IV}R^V$, wherein $R^{IV}$ and $R^V$ are independently hydrogen, lower alkyl of 1 to 6 carbon atoms, or aminoalkyl of 1 to 6 carbon atoms, provided that $R^{IV}$ and $R^V$ may not both be aminoalkyl; CN; $CO_2R^{VI}$, wherein $R^{VI}$ is hydrogen or lower alkyl of 1 to 6 carbon atoms; and $C(O)NR^{VII}R^{VIII}$, wherein $R^{VII}$ and $R^{VIII}$ are independently hydrogen, lower alkyl of 1 to 6 carbon atoms or aminoalkyl of 1 to 6 carbon atoms, provided that $R^{VII}$ and $R^{VIII}$ may not both by aminoalkyl;

$R_1$ and $R_2$ are independently hydrogen, hydroxy, lower alkyl having 1 to 6 carbon atoms, or lower alkoxy having 1 to 6 carbon atoms; $R_3$ and $R_4$ are independently hydrogen or lower alkyl having 1 to 6 carbon atoms and each $R_3$ and $R_4$ is independently selected in each $-O-CHR_3-CHR_4-$ unit; $R_5$ is hydrogen, alkyl having 1 to 100 carbon atoms, phenyl, aralkyl having 7 to 100 carbon atoms or alkaryl having 7 to 100 carbon atoms, or an acyl group of the formula:

(II)

wherein $R_6$ is alkyl having 1 to 30 carbon atoms, phenyl, aralkyl having 7 to 36 carbon atoms or alkaryl having 7 to 36 carbon atoms; n is an integer from 5 to 100; and x is an integer from 0 to 10.

The present invention further provides a fuel composition comprising a major amount of hydrocarbons boiling in the gasoline or diesel range and an effective deposit-controlling amount of a substituted poly(oxyalkylene) aromatic ether of the present invention.

The present invention additionally provides a fuel concentrate comprising an inert stable oleophilic organic solvent boiling in the range of from about 150° F. (65° C.) to 400° F. (205° C.) and from about 10 to 70 weight percent of a substituted poly(oxyalkylene) aromatic ether of the present invention.

Among other factors, the present invention is based on the discovery that certain poly(oxyalkylene) aromatic ethers which are substituted on the aromatic moiety are surprisingly useful for reducing engine deposits, especially on intake valves, when employed as fuel additives in fuel compositions.

DETAILED DESCRIPTION OF THE INVENTION

The fuel additives provided by the present invention have the general formula:

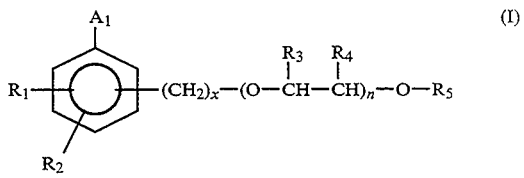

(I)

wherein $A_1$, $R_1$, $R_2$, $R_3$, $R_4$, $R_5$, n and x are as defined above.

In formula I, above, $A_1$ may be a thioether, $SR^I$, a sulfoxide, $SOR^{II}$, a sulfone, $SO_2R^{III}$, a sulfonic acid, $SO_3H$, a sulfonamide, $SO_2NR^{IV}R^V$, a nitrile(cyano), CN, a carboxylic acid or ester, $CO_2R^{VI}$, or a carboxamide, $C(O)NR^{VII}R^{VIII}$.

Preferably, $A_1$ is a thioether, $SR^I$, a sulfone, $SO_2R^{III}$, a nitrile, CN, a carboxylic acid or ester, $CO_2R^{VI}$, or a carboxamide, $C(O)NR^{VII}R^{VIII}$. More preferably, $A_1$ is a thioether, $SR^I$, a sulfone, $SO_2R^{III}$, or a nitrile, CN.

Preferably, $R_1$ is hydrogen, hydroxy, or lower alkyl having 1 to 4 carbon atoms. More preferably, $R_1$ is hydrogen or hydroxy. Most preferably, $R_1$ is hydrogen.

$R_2$ is preferably hydrogen.

Preferably, one of $R_3$ and $R_4$ is lower alkyl having 1 to 3 carbon atoms and the other is hydrogen. More preferably, one of $R_3$ and $R_4$ is methyl or ethyl and the other is hydrogen. Most preferably, one of $R_3$ and $R_4$ is ethyl and the other is hydrogen.

$R_5$ is preferably hydrogen, alkyl having 1 to 30 carbon atoms, or alkylphenyl having an alkyl group containing 1 to 30 carbon atoms. More preferably, $R_5$ is hydrogen, alkyl having 2 to 24 carbon atoms, or alkylphenyl having an alkyl group containing 2 to 24 carbon atoms. Still more preferably, $R_5$ is hydrogen, alkyl having 4 to 12 carbon atoms or alkylphenyl having an alkyl group containing 4 to 12 carbon atoms. Most preferably, $R_5$ is alkylphenyl having an alkyl group containing 4 to 12 carbon atoms.

$R_6$ is preferably alkyl having 4 to 12 carbon atoms.

Preferably, n is an integer from 8 to 50. More preferably, n is an integer from 10 to 30. Preferably, x is an integer from 0 to 2. Most preferably, x is 0.

A preferred group of substituted poly(oxyalkylene) aromatic ethers of the invention are compounds of formula I wherein $R_1$ is hydrogen or hydroxy; $R_2$ is hydrogen; one of $R_3$ and $R_4$ is hydrogen and the other is methyl or ethyl; $R_5$ is hydrogen, alkyl having 1 to about 30 carbon atoms or alkylphenyl having an alkyl group containing 1 to about 30 carbon atoms; n is 8 to 50 and x is 0, 1 or 2.

A more preferred group of substituted poly(oxyalkylene) aromatic ethers are those of formula I wherein $R_1$ is hydrogen or hydroxy; $R_2$ is hydrogen; one of $R_3$ and $R_4$ is hydrogen and the other is methyl or ethyl; $R_5$ is hydrogen, alkyl having 2 to 24 carbon atoms or alkylphenyl having an alkyl group containing 2 to 24 carbon atoms; n is 8 to 50; and x is 0.

It is especially preferred that the $A_1$ substituent present in the aromatic moiety of the poly(oxyalkylene) aromatic ethers of this invention be situated in a meta or para position relative to the poly(oxyalkylene) ether moiety. When the aromatic moiety also contains a hydroxyl substituent, it is particularly preferred that this hydroxyl group be in a meta or para position relative to the poly(oxyalkylene) ether moiety and in an ortho position relative to the $A_1$ substituent.

The poly(oxyalkylene) aromatic ethers employed in the present invention will generally have a sufficient molecular weight so as to be non-volatile at normal engine intake valve operating temperatures (about 200°–250° C.). Typically, the molecular weight of the poly(oxyalkylene) aromatic ethers will range from about 600 to about 10,000, preferably from about 1,000 to 3,000.

Generally, the poly(oxyalkylene) aromatic ethers employed in this invention will contain an average of about 5 to about 100 oxyalkylene units; preferably, 8 to 50 oxyalkylene units; more preferably, 10 to 30 oxyalkylene units.

Fuel-soluble salts of the poly(oxyalkylene) aromatic ethers of the present invention can be readily prepared for those compounds containing an amino group and such salts are contemplated to be useful for preventing or controlling engine deposits. Suitable salts include, for example, those obtained by protonating the amino moiety with a strong organic acid, such as an alkyl- or arylsulfonic acid. Preferred salts are derived from toluenesulfonic acid and methanesulfonic acid.

Definitions

As used herein, the following terms have the following meanings unless expressly stated to the contrary.

The term "amino" refers to the group: $-NH_2$.

The term "alkyl" refers to both straight- and branched-chain alkyl groups.

The term "lower alkyl" refers to alkyl groups having 1 to about 6 carbon atoms and includes primary, secondary and tertiary alkyl groups. Typical lower alkyl groups include, for example, methyl, ethyl, n-propyl, isopropyl, n-butyl, sec-butyl, t-butyl, n-pentyl, n-hexyl and the like.

The term "lower alkoxy" refers to the group $-OR_d$ wherein $R_d$ is lower alkyl. Typical lower alkoxy groups include methoxy, ethoxy, and the like.

The term "alkaryl" refers to the group:

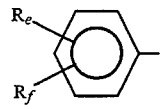

wherein $R_e$ and $R_f$ are each independently hydrogen or an alkyl group, with the proviso that both $R_e$ and $R_f$ are not hydrogen. Typical alkaryl groups include, for example, tolyl, xylyl, cumenyl, ethylphenyl, butylphenyl, dibutylphenyl, hexylphenyl, octylphenyl, dioctylphenyl, nonylphenyl, decylphenyl, didecylphenyl, dodecylphenyl, hexadecylphenyl, octadecylphenyl, icosylphenyl, tricontylphenyl and the like. The term "alkylphenyl" refers to an alkaryl group of the above formula in which $R_e$ is alkyl and $R_f$ is hydrogen.

The term "aralkyl" refers to the group:

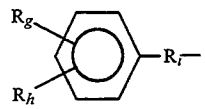

wherein $R_g$ and $R_h$ are each independently hydrogen or an alkyl group; and $R_i$ is an alkylene group. Typical alkaryl groups include, for example, benzyl, methylbenzyl, dimethylbenzyl, phenethyl, and the like.

The term "oxyalkylene unit" refers to an ether moiety having the general formula:

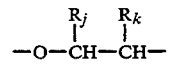

wherein $R_j$ and $R_k$ are each independently hydrogen or lower alkyl groups.

The term "poly(oxyalkylene)" refers to a polymer or oligomer having the general formula:

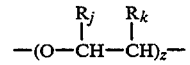

wherein $R_j$ and $R_k$ are as defined above, and z is an integer greater than 1. When referring herein to the number of poly(oxyalkylene) units in a particular poly(oxyalkylene) compound, it is to be understood that this number refers to the average number of poly(oxyalkylene) units in such compounds unless expressly stated to the contrary.

General Synthetic Procedures

The poly(oxyalkylene) aromatic ethers of the present invention can be prepared by the following general methods and procedures. Those skilled in the art will recognize that where typical or preferred process conditions (e.g., reaction temperatures, times, mole ratios of reactants, solvents, pressures, etc.) are given, other process conditions may also be used unless otherwise stated. Optimum reaction conditions may vary with the particular reactants or solvents used, but one skilled in the art will be able to determine such conditions by routine optimization procedures.

Moreover, those skilled in the art will recognize that it may be necessary to block or protect certain functional groups while conducting the following synthetic procedures. In such cases, the protecting group will serve to protect the functional group from undesired reactions or to block its undesired reaction with other functional groups or with the reagents used to carry out the desired chemical transformations. The proper choice of a protecting group for a particular functional group will be readily apparent to one skilled in the art. Various protecting groups and their introduction and removal are described, for example, in T. W. Greene and P. G. M. Wuts, *Protective Groups in Organic Synthesis*, Second Edition, Wiley, N.Y., 1991, and references cited therein.

In the present synthetic procedures, a hydroxyl group, if present, will preferably be protected, when necessary, as the benzyl or tert-butyldimethylsilyl ether. Introduction and removal of these protecting groups is well described in the art.

The poly(oxyalkylene) aromatic ethers of the present invention may be prepared from an aromatic compound having the formula:

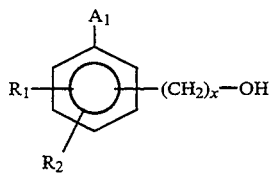
(III)

wherein $A_1$, $R_1$, $R_2$, and x are as defined above.

The aromatic compounds of formula III are either known compounds or can be prepared from known compounds by conventional procedures. Aromatic compounds suitable for use as starting materials in this invention include, for example, 4-methylmercaptophenol, 4-cyanophenol, 4-hydroxybenzamide, tert-butyl-4-hydroxybenzoate, and the like.

Preferred aromatic compounds of formula III include 4-methylmercaptophenol and 4-cyanophenol.

Alternatively, substituent $A_1$ can be further modified by conventional procedures well known to those skilled in the art to provide additional aromatic compounds encompassed by formula III, above.

In a preferred method of synthesizing the poly(oxyalkylene) aromatic ethers of the present invention, an aromatic compound of formula III is deprotonated with a suitable base to provide a metal salt having the formula:

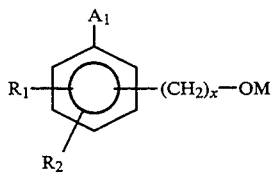
(IV)

wherein $A_1$, $R_1$, $R_2$ and x are as defined above; and M is a metal cation, such as lithium, sodium or potassium.

Generally, this deprotonation reaction will be effected by contacting III with a strong base, such as sodium hydride, potassium hydride, sodium amide and the like, in an inert solvent, such as toluene, xylene and the like, under substantially anhydrous conditions at a temperature in the range from about $-10°$ C. to about $120°$ C. for about 0.25 to about 3 hours.

Metal salt IV is generally not isolated, but is reacted in situ with a poly(oxyalkylene) derivative having the formula:

(V)

wherein $R_3$, $R_4$, n and x are as defined above, $R_9$ is an alkyl, phenyl, aralkyl or alkaryl group, and W is a suitable leaving group, such as a sulfonate or a halide, to provide a poly(oxyalkylene) aromatic ether of the formula:

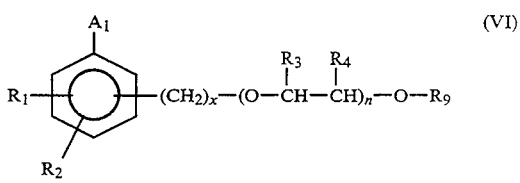
(VI)

wherein $A_1$, $R_1$-$R_4$, $R_9$, n and x are as defined above.

Generally, this reaction will be conducted by contacting V with 0.8 to 5 molar equivalents of IV in an inert solvent, such as toluene, tetrahydrofuran and the like, under substantially anhydrous conditions at a temperature in the range of about 25° C. to about 150° C. for about 1 to about 48 hours.

The poly(oxyalkylene) derivative V may be derived from a poly(oxyalkylene) alcohol having the formula:

(VII)

wherein $R_3$, $R_4$, $R_9$, n and x are as defined above.

The hydroxyl group of the poly(oxyalkylene) moiety of VII may be converted into a suitable leaving group by contacting VII with a sulfonyl chloride to form a sulfonate ester, such as a methanesulfonate (mesylate) or a toluenesulfonate (tosylate). Typically, this reaction is conducted in the presence of a suitable amine, such as triethylamine or pyridine, in an inert solvent, such as dichloromethane, at a temperature in the range of about $-10°$ C. to about 30° C. Alternatively, the hydroxyl group of the poly(oxyalkylene) moiety of VII can be exchanged for a halide, such chloride or bromide, by contacting VII with a halogenating agent, such as thionyl chloride, oxalyl chloride or phosphorus tribromide. Other suitable methods for preparing sulfonates and halides from alcohols, and appropriate reaction conditions for such reactions, can be found, for example, in I. T. Harrison and S. Harrison, *Compendium of Organic Synthetic Methods*, Vol. 1, pp. 331–337, Wiley-Interscience, New York (1971) and references cited therein.

The poly(oxyalkylene) alcohols of formula VII are known compounds that can be prepared using conventional procedures. For example, suitable procedures for preparing such compounds are taught in U.S. Pat. Nos. 2,782,240 and 02 2,841,479, the disclosures of which are incorporated herein by reference.

Preferably, the poly(oxyalkylene) alcohols of formula V are prepared by contacting an alkoxide or phenoxide metal salt having the formula:

$$R_9OM \quad (VIII)$$

wherein $R_9$ is as defined above and M is a metal cation, such as lithium, sodium, potassium and the like, with about 5 to about 100 molar equivalents of an alkylene oxide (an epoxide) having the formula:

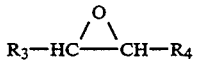

(IX)

wherein $R_3$ and $R_4$ are as defined above.

Typically, metal salt VIII is prepared by contacting the corresponding hydroxy compound $R_9OH$ with a strong base, such as sodium hydride, potassium hydride, sodium amide and the like, in an inert solvent, such as toluene, xylene and the like, under substantially anhydrous conditions at a temperature in the range from about $-10°$ C. to about $120°$ C. for about 0.25 to about 3 hours.

Metal salt VIII is generally not isolated, but is reacted in situ with alkylene oxide IX to provide, after neutralization, the poly(oxyalkylene) alcohol VII. This polymerization reaction is typically conducted in a substantially anhydrous inert solvent at a temperature of about $30°$ C. to about $150°$ C. for about 2 to about 120 hours. Suitable solvents for this reaction, include toluene, xylene and the like. Typically, the reaction is conducted at a pressure sufficient to contain the reactants and the solvent, preferably at atmospheric or ambient pressure.

The amount of alkylene oxide employed in this reaction will generally depend on the number of oxyalkylene units desired in the product. Typically, the molar ratio of alkylene oxide IX to metal salt VIII will range from about 5:1 to about 100:1; preferably, from 8:1 to 50:1, more preferably from 10:1 to 30:1.

Alkylene oxides suitable for use in this polymerization reaction include, for example, ethylene oxide; propylene oxide; butylene oxides, such as 1,2-butylene oxide (1,2-epoxybutane) and 2,3-butylene oxide (2,3-epoxybutane); pentylene oxides; hexylene oxides; octylene oxides and the like. Preferred alkylene oxides are propylene oxide and 1,2-butylene oxide.

In the polymerization reaction, a single type of alkylene oxide may be employed, e.g., propylene oxide, in which case the product is a homopolymer, e.g., a poly(oxypropylene) polymer. Copolymers are equally satisfactory and random copolymers can be prepared by contacting metal salt VI with a mixture of alkylene oxides, such as a mixture of propylene oxide and 1,2-butylene oxide, under polymerization conditions. Copolymers containing blocks of oxyalkylene units are also suitable for use in this invention. Block copolymers can be prepared by contacting metal salt VI with first one alkylene oxide, then others in any order, or repetitively, under polymerization conditions.

Poly(oxyalkylene) copolymers prepared by terminating or capping the poly(oxyalkylene) moiety with 1 to 10 oxyethylene units, preferably. 2 to 5 oxyethylene units, are particularly useful in the present invention, since these copolymers have been found to be more readily converted into an aromatic ether than those having an alkyl branch in the terminal oxyalkylene unit. These copolymers may be prepared by contacting metal salt VIII with an alkylene oxide of formula IX, such as 1,2-butylene oxide or propylene oxide, under polymerization conditions and then capping or terminating the resulting block of oxyalkylene units with oxyethylene units by adding ethylene oxide.

The poly(oxyalkylene) alcohol VII may also be prepared by living or immortal polymerization as described by S. Inoue and T. Aida in Encyclopedia of Polymer Science and Engineering, Second Edition, Supplemental Volume, J. Wiley and Sons, New York, pages 412-420 (1989). These procedures are especially useful for preparing poly(oxyalkylene) alcohols of formula VII in which $R_3$ and $R_4$ are both alkyl groups.

As noted above, the alkoxide or phenoxide metal salt VIII used in the above procedures is generally derived from the corresponding hydroxy compound, $R_9OH$. Suitable hydroxy compounds include straight- or branched-chain aliphatic alcohols having 1 to about 100 carbon atoms and phenols having the formula:

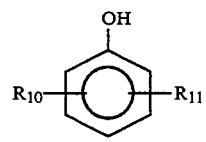

(X)

wherein $R_{10}$ is an alkyl group having 1 to about 100 carbon atoms and $R_{11}$ is hydrogen; or $R_{10}$ and $R_{11}$ are both alkyl groups, each independently containing 1 to about 50 carbon atoms.

Representative examples of straight- or branched-chain aliphatic alcohols suitable for use in this invention include, but are not limited to, n-butanol; isobutanol; sec-butanol; t-butanol; n-pentanol; n-hexanol; n-heptanol; n-octanol; isooctanol; n-nonanol; n-decanol; n-dodecanol; n-hexadecanol (cetyl alcohol); n-octadecanol (stearyl alcohol); alcohols derived from linear $C_{10}$ to $C_{30}$ alpha olefins and mixtures thereof; and alcohols derived from polymers of $C_2$ to $C_6$ olefins, such as alcohols derived from polypropylene and polybutene, including polypropylene alcohols having 9 to about 100 carbon atoms and polybutylene alcohols having 12 to about 100 carbon atoms. Preferred straight- or branched-chain aliphatic alcohols will contain 1 to about 30 carbon atoms, more preferably 2 to about 24 carbon atoms, and most preferably 4 to 12 carbon atoms. Particularly, preferred aliphatic alcohols are butanols.

The phenols of formula X may be monoalkyl-substituted phenols or dialkyl-substituted phenols. Monoalkyl-substituted phenols are preferred, especially monoalkylphenols having an alkyl substituent in the para position.

Preferably, the alkyl group of the alkylphenol will contain 1 to about 30 carbon atoms, more preferably 2 to 24 carbon atoms, and most preferably 4 to 12 carbon atoms. Representative examples of phenols suitable for use in this invention include, but are not limited to, phenol, methylphenol, dimethylphenol, ethylphenol, butylphenol, octylphenol, decylphenol, dodecylphenol, tetradecylphenol, hexadecylphenol, octadecylphenol, eicosylphenol, tetracosylphenol, hexacosylphenol, triacontylphenol and the like. Also, mixtures of alkylphenols may be employed, such as a mixture of $C_{14}$–$C_{18}$ alkylphenols, a mixture of $C_{18}$–$C_{24}$ alkylphenols, a mixture of $C_{20}$–$C_{24}$ alkylphenols, or a mixture of $C_{16}$–$C_{26}$ alkylphenols.

Particularly, preferred alkylphenols are prepared by alkylating phenol with polymers or oligomers of $C_3$ to $C_6$ olefins, such as polypropylene or polybutene. These polymers typically contain 8 to about 100 carbon atoms, preferably 10 to 30 carbon atoms. An especially preferred alkylphenol is prepared by alkylating phenol with a propylene polymer having an average of 4 units. This polymer has the common name of propylene tetramer and is commercially available.

The poly(oxyalkylene) aromatic ethers of formula I wherein $R_5$ is hydrogen, i.e., compounds having the formula:

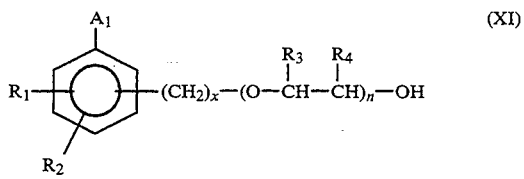
(XI)

wherein $A_1$, $R_1$–$R_4$, n and x are as defined above, may be prepared from compounds of formula VI wherein $R_9$ is a labile hydrocarbyl group, such as a benzyl or t-butyl group, by removing the hydrocarbyl group under appropriate conditions to provide a hydroxyl group. For example, compounds of formula VI where $R_9$ represents a benzyl group may be prepared by employing a metal salt VIII derived from benzyl alcohol in the above-described synthetic procedures. Cleavage of the benzyl ether using conventional hydrogenolysis procedures then provides a compound of formula XI. Other labile hydrocarbyl groups, such as a t-butyl group, may be similarly employed for those compounds having functional groups that are not compatible with hydrogenolysis conditions, such as nitro groups. t-Butyl ethers may be cleaved under acidic conditions using, for example, trifluoroacetic acid.

Alternatively, the poly(oxyalkylene) aromatic ethers of formula XI may be prepared by reacting metal salt IV with an alkylene oxide of formula IX. The conditions for this reaction are essentially the same as those described above for the preparation of poly(oxyalkylene) alcohol VII. If desired, the hydroxyl group of XI may be alkylated using well known procedures to provide a poly(oxyalkylene) aromatic ether of formula I wherein $R_5$ is an alkyl or aralkyl group. Additionally, the hydroxyl group of XI may be converted into a leaving group using essentially the same procedures as those described above for the preparation of V, and this leaving group may be displaced with the metal salt of phenol X using conventional procedures to provide a poly(oxyalkylene) aromatic ether of formula I wherein $R_5$ is an alkaryl group.

The poly(oxyalkylene) aromatic ethers of the present invention containing an acyl moiety, i.e., those having the formula:

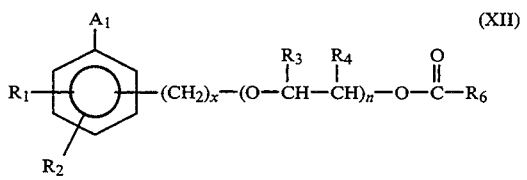
(XII)

wherein $A_1$, $R_1$–$R_4$, $R_6$, n and x are as defined above; may be prepared from XI by acylating the hydroxyl group of the poly(oxyalkylene) moiety of XI to form an ester.

Generally, this acylation reaction will be conducted by contacting XI with about 0.95 to about 1.2 molar equivalents of a suitable acylating agent. Suitable acylating agents for use in this reaction include acyl halides, such as acyl chlorides and bromides; and carboxylic acid anhydrides. Preferred acylating agents are those having the formula:

$R_6C(O)$—X, wherein $R_6$ is alkyl having 1 to 30 carbon atoms, phenyl, or aralkyl or alkaryl having 7 to 36 carbon atoms, and X is chloro or bromo. More preferably, $R_6$ is alkyl having 4 to 12 carbon atoms. Representative examples of suitable acylating agents include, but are not limited to, acetyl chloride, acetic anhydride, propionyl chloride, butanoyl chloride, pivaloyl chloride, octanoyl chloride, decanoyl chloride 4-t-butylbenzoyl chloride and the like.

Generally, this reaction is conducted in an inert solvent, such as toluene, dichloromethane, diethyl ether and the like, at a temperature in the range of about 25° C. to about 150° C., and is generally complete in about 0.5 to about 48 hours. When an acyl halide is employed as the acylating agent, this reaction is preferably conducted in the presence of a sufficient amount of an amine capable of neutralizing the acid generated during the reaction, such as triethylamine, di(isopropyl)ethylamine, pyridine or 4-dimethylaminopyridine.

Additional methods for preparing esters from alcohols, and suitable reaction conditions for such reactions, can be found, for example, in I. T. Harrison and S. Harrison, *Compendium of Organic Synthetic Methods*, Vol. 1, pp. 273–276 and 280–283, Wiley-Interscience, New York (1971) and references cited therein.

Fuel Compositions

The poly(oxyalkylene) aromatic ethers of the present invention are useful as additives in hydrocarbon fuels to prevent and control engine deposits, particularly intake valve deposits. Typically, the desired deposit control is achieved by operating an internal combustion engine with a fuel composition containing a poly(oxyalkylene) aromatic ether of the present invention. The proper concentration of additive necessary to achieve the desired level of deposit control varies depending upon the type of fuel employed, the type of engine, and the presence of other fuel additives.

In general, the concentration of the poly(oxyalkylene) aromatic ethers of this invention in hydrocarbon fuel will range from about 50 to about 2500 parts per million (ppm) by weight, preferably from 75 to 1,000 ppm. When other deposit control additives are present, a lesser amount of the present additive may be used.

The poly(oxyalkylene) aromatic ethers of the present invention may also be formulated as a concentrate using an inert stable oleophilic (i.e., dissolves in gasoline) organic solvent boiling in the range of about 150° F. to 400° F. (about 65° C. to 205° C.). Preferably, an aliphatic or an aromatic hydrocarbon solvent is used, such as benzene, toluene, xylene or higher-boiling aromatics or aromatic thinners. Aliphatic alcohols containing about 3 to 8 carbon atoms, such as isopropanol, isobutylcarbinol, n-butanol and the like, in combination with hydrocarbon solvents are also suitable for use with the present additives. In the concentrate, the amount of the additive will generally range from about 10 to about 70 weight percent, preferably 10 to 50 weight percent, more preferably from 20 to 40 weight percent.

In gasoline fuels, other fuel additives may be employed with the additives of the present invention, including, for example, oxygenates, such as t-butyl methyl ether, antiknock agents, such as methylcyclopentadienyl manganese tricarbonyl, and other dispersants/detergents, such as hydrocarbyl amines, hydrocarbyl poly(oxyalkylene) amines, or succinimides. Additionally, antioxidants, metal deactivators and demulsifiers may be present.

In diesel fuels, other well-known additives can be employed, such as pour point depressants, flow improvers, cetane improvers, and the like.

A fuel-soluble, nonvolatile carrier fluid or oil may also be used with the poly(oxyalkylene) aromatic ethers of this invention. The carrier fluid is a chemically inert hydrocarbon-soluble liquid vehicle which substantially increases the nonvolatile residue (NVR), or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, including hydrogenated and unhydrogenated polyalphaolefins, synthetic polyoxyalkylene-derived oils, such as those described, for example, in U.S. Pat. No. 4,191,537 to Lewis, and polyesters, such as those described, for example, in U.S. Pat. Nos. 3,756,793 and 5,004,478 to Robinson and Vogel et al., respectively, and in European Patent Application Nos. 356,726 and 382,159, published Mar. 7, 1990 and Aug. 16, 1990, respectively.

These carrier fluids are believed to act as a carrier for the fuel additives of the present invention and to assist in removing and retarding deposits. The carrier fluid may also exhibit synergistic deposit control properties when used in combination with a poly(oxyalkylene) aromatic ether of this invention.

The carrier fluids are typically employed in amounts ranging from about 100 to about 5000 ppm by weight of the hydrocarbon fuel, preferably from 400 to 3000 ppm of the fuel. Preferably, the ratio of carrier fluid to deposit control additive will range from about 0.5:1 to about 10:1, more preferably from 1:1 to 4:1, most preferably about 2:1.

When employed in a fuel concentrate, carrier fluids will generally be present in amounts ranging from about 20 to about 60 weight percent, preferably from 30 to 50 weight percent.

EXAMPLES

The following examples are presented to illustrate specific embodiments of the present invention and synthetic preparations thereof; and therefore these examples should not be interpreted as limitations upon the scope of this invention.

Example 1

Preparation of
α-(Methanesulfonyl)-ω-4-dodecylphenoxypoly(oxybutylene)

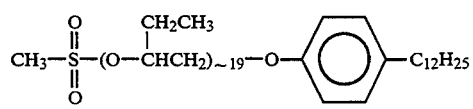

To a flask equipped with a magnetic stirrer, septa and a nitrogen inlet was added 244.8 grams of α-hydroxy-ω-4-dodecylphenoxypoly(oxybutylene) having an average of 19 oxybutylene units (prepared essentially as described in Example 6 of U.S. Pat. No. 4,160,648), 400 mL of dichloromethane and 26.5 mL of triethylamine. The flask was cooled in an ice bath and 14.9 mL of methanesulfonyl chloride were added dropwise. The ice bath was removed and the reaction was stirred at room temperature for 16 hours. Dichloromethane (1.2 L) was added and the organic phase was washed two times with saturated aqueous sodium bicarbonate, and then once with brine. The organic layer was dried over anhydrous magnesium sulfate, filtered and concentrated in vacuo to yield 265.0 grams of the desired product as a yellow oil.

Example 2

Preparation of
α-(4-Methylmercaptophenyl)-ω-4-dodecylphenoxypoly(oxybutylene)

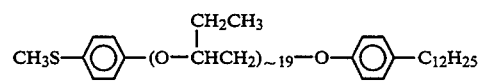

To a flask equipped with a magnetic stirrer, reflux condenser, nitrogen inlet and addition funnel was added 2.5 grams of a 35 weight percent dispersion of potassium hydride in mineral oil. 4-Methylmercaptophenol (2.8 grams) dissolved in 25 mL of anhydrous tetrahydrofuran was added dropwise and the reaction was allowed to stir at room temperature for two hours. The mesylate from Example 1 (33.9 grams) was dissolved in 100 mL of anhydrous tetrahydrofuran and added to the reaction mixture. The resulting mixture was refluxed for 16 hours, cooled to room temperature and 10 mL of methanol were added. The reaction was diluted with 300 mL of diethyl ether and washed with 5% aqueous sodium hydroxide, followed by saturated aqueous sodium chloride solution. The organic layer was then dried over anhydrous magnesium sulfate, filtered and the solvents removed in vacuo to yield an oil. The oil was chromatographed on silica gel, eluting with hexane/diethyl ether (1:1) to yield 30.0 grams of the desired product as a yellow oil. The product had an average of 19 oxybutylene units. $^1$H NMR (CDCl$_3$)$\delta$ 7.2, 6.85 (AB quartet, 4H), 7.1–7.3 (m, 2H), 6.75–6.95 (m, 2H), 4.2–4.3 (m, 1H), 3.85–4.0 (m, 2H), 3.1–3.85 (m, 54H), 2.4 (s, 3H), 0.6–1.8 (m, 120H).

Example 3

Preparation of
α-(4-Cyanophenyl)-ω-4-dodecylphenoxypoly(oxybutylene)

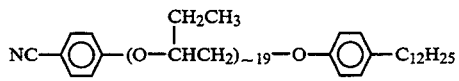

To a flask equipped with a magnetic stirrer, reflux condenser, nitrogen inlet and addition funnel was added 0.66 grams of an 80 weight percent dispersion of sodium hydride in mineral oil. 4-Cyanophenol (2.3 grams) dissolved in 125 mL of anhydrous N,N-dimethylformamide was added dropwise and the reaction was allowed to stir at room temperature for two hours. The mesylate from Example 1 (33.9 grams) was dissolved in 25 mL of anhydrous N,N-dimethylformamide and added to the reaction mixture. The resulting mixture was refluxed for 48 hours, cooled to room temperature and 10 mL of methanol were added. The reaction was diluted with 300 mL of diethyl ether and washed with 5% aqueous sodium hydroxide, followed by saturated aqueous sodium chloride solution. The organic layer was then dried over anhydrous magnesium sulfate, filtered and the solvents removed in vacuo to yield 30 grams as an oil. The oil was chromatographed on silica gel, eluting with hexane/diethyl ether (1:1) to yield 24.0 grams of the desired product as a yellow oil. The product had an average of 19 oxybutylene units. $^1$H NMR (CDCl$_3$)$\delta$ 7.55, 7.0 (AB quartet, 4H), 7.1–7.3 (m, 2H), 6.75–6.95 (m, 2H), 4.35–4.45 (m, 1H), 3.85–4.0 (m, 2H), 3.1–3.85 (m, 54H), 2.35 (s, 3H), 0.6–1.8 (m, 120H).

Example 4

Preparation of
α-(4-Methylsulfonylphenyl)-ω-4-dodecylphenoxypoly(oxybutylene)

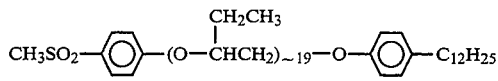

To a flask equipped with a magnetic stirrer, thermometer and nitrogen inlet was added powdered potassium permaganate (5.0 grams) and acetone (50 mL). The contents of the flask were cooled to 0° C. and α-(4-methylmercaptophenyl)-ω-4-dodecylphenoxypoly(oxybutylene) (14.0 grams, from Example 2) dissolved in 50 mL of acetone was added. The reaction was stirred at room temperature for 16 hours, filtered and the solvents removed in vacuo. The oil was chromatographed on silica gel, eluting with hexane/diethyl ether (1:1) to yield 14.0 grams of the desired product as a colorless oil. The product had an average of 19 oxybutylene units. $^1$H NMR (CDCl$_3$)$\delta$ 7.8, 7.1 (AB quartet, 4H), 7.1–7.3 (m, 2H), 6.75–6.95 (m, 2H), 4.35–4.45 (m, 1H), 3.85–4.0 (m, 2H), 3.1–3.85 (m, 54H), 3.0 (s, 3H), 0.6–1.8 (m, 120H).

Example 5

Single-Cylinder Engine Test

The test compounds were blended in gasoline and their deposit reducing capacity determined in an ASTM/CFR single-cylinder engine test.

A Waukesha CFR single-cylinder engine was used. Each run was carried out for 15 hours, at the end of which time the intake valve was removed, washed with hexane and weighed. The previously determined weight of the clean valve was subtracted from the weight of the value at the end of the run. The differences between the two weights is the weight of the deposit. A lesser amount of deposit indicates a superior additive. The operating conditions of the test were as follows: water jacket temperature 200° F.; vacuum of 12 in Hg, air-fuel ratio of 12, ignition spark timing of 40° BTC; engine speed is 1800 rpm; the crankcase oil is a commercial 30 W oil.

The amount of carbonaceous deposit in milligrams on the intake valves is reported for each of the test compounds in Table I.

TABLE I

| Sample[1] | Intake Valve Deposit Weight (in milligrams) | | |
|---|---|---|---|
| | Run 1 | Run 2 | Average |
| Base Fuel | 302.6 | 312.2 | 307.4 |
| Example 2 | 54.0 | 78.2 | 66.1 |
| Example 3 | 124.9 | 165.0 | 145.0 |
| Example 4 | 110.0 | 96.6 | 103.3 |

[1]At 200 parts per million actives (ppma).

The base fuel employed in the above single-cylinder engine tests was a regular octane unleaded gasoline containing no fuel detergent. The test compounds were admixed with the base fuel to give a concentration of 200 ppma (parts per million actives).

The data in Table I illustrates the significant reduction in intake valve deposits provided by the poly(oxyalkylene) aromatic ethers of the present invention (Examples 2, 3 and 4) compared to the base fuel.

What is claimed is:

1. A compound of the formula:

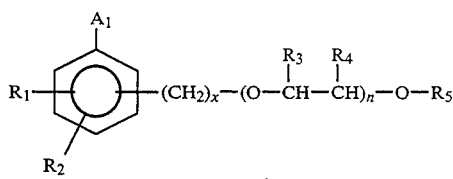

wherein A$_1$ is selected from the group consisting of SR$^I$, SOR$^{II}$, SO$_2$R$^{III}$, wherein R$^I$, R$^{II}$ and R$^{III}$ are independently lower alkyl of 1 to 6 carbon atoms; SO$_2$NR$^{IV}$R$^V$, wherein R$^{IV}$ and R$^V$ are independently hydrogen, lower alkyl of 1 to 6 carbon atoms, or aminoalkyl of 1 to 6 carbon atoms, provided that R$^{IV}$ and R$^V$ may not both be aminoalkyl; CN; and C(O)NR$^{VII}$R$^{VIII}$, wherein R$^{VII}$ and R$^{VIII}$ are independently hydrogen, lower alkyl of 1 to 6 carbon atoms or aminoalkyl of 1 to 6 carbon atoms, provided that R$^{VII}$ and R$^{VIII}$ may not both by aminoalkyl;

R$_1$ and R$_2$ are independently hydrogen, hydroxy, lower alkyl having 1 to 6 carbon atoms, or lower alkoxy having 1 to 6 carbon atoms;

R$_3$ and R$_4$ are independently hydrogen or lower alkyl having 1 to 6 carbon atoms and each R$_3$ and R$_4$ is independently selected in each —O—CHR$_3$—CHR$_4$— unit;

R$_5$ is hydrogen, alkyl having 1 to 100 carbon atoms, phenyl, aralkyl having 7 to 100 carbon atoms, alkaryl having 7 to 100 carbon atoms, or an acyl group having the formula:

wherein R$_6$ is alkyl having 1 to 30 carbon atoms, phenyl, aralkyl having 7 to 36 carbon atoms or alkaryl having 7 to 36 carbon atoms;

n is an integer from 5 to 100; and x is an integer from 0 to 10.

2. The compound according to claim 1, wherein n is an integer ranging from 8 to 50.

3. The compound according to claim 2, wherein n is an integer ranging from 10 to 30.

4. The compound according to claim 2, wherein $R_1$ is hydrogen, hydroxy, or lower alkyl having 1 to 4 carbon atoms; and $R_2$ is hydrogen.

5. The compound according to claim 4, wherein $R_5$ is hydrogen, alkyl having 1 to 30 carbon atoms, or alkylphenyl having an alkyl group containing 1 to 30 carbon atoms.

6. The compound according to claim 5, wherein $R_1$ is hydrogen or hydroxy.

7. The compound according to claim 6, wherein $A_1$ is selected from the group consisting of $SR^I$, $SO_2R^{III}$, CN and $C(O)NR^{VII}R^{VII}$.

8. The compound according to claim 7, wherein $R_5$ is hydrogen, alkyl having 2 to 24 carbon atoms, or alkylphenyl having an alkyl group containing 2 to 24 carbon atoms.

9. The compound according to claim 8, wherein one of $R_3$ and $R_4$ is lower alkyl having 1 to 3 carbon atoms and the other is hydrogen.

10. The compound according to claim 9, wherein one of $R_3$ and $R_4$ is methyl or ethyl and the other is hydrogen.

11. The compound according to claim 10, wherein x is 0, 1 or 2.

12. The compound according to claim 11, wherein $R_1$ is hydrogen, $R_5$ is alkylphenyl having an alkyl group containing 4 to 12 carbon atoms, and x is 0.

13. The compound according to claim 12, wherein $A_1$ is $SR^I$, $SO_2R^{III}$ or CN.

14. A fuel composition comprising a major amount of hydrocarbons boiling in the gasoline or diesel range and an effective detergent amount of a compound of the formula:

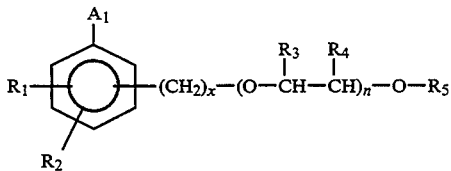

wherein $A_1$ is selected from the group consisting of $SR^I$, $SOR^{II}$, $SO_2R^{III}$, wherein $R^I$, $R^{II}$ and $R^{III}$ are independently lower alkyl of 1 to 6 carbon atoms; $SO_3H$; $SO_2NR^{IV}R^V$, wherein $R^{IV}$ and $R^V$ are independently hydrogen, lower alkyl of 1 to 6 carbon atoms, or aminoalkyl of 1 to 6 carbon atoms, provided that $R^{IV}$ and $R^V$ may not both be aminoalkyl; CN; $CO_2R^{VI}$, wherein $R^{VI}$ is hydrogen or lower alkyl of 1 to 6 carbon atoms; and $C(O)NR^{VII}R^{VIII}$, wherein $R^{VII}$ and $R^{VIII}$ are independently hydrogen, lower alkyl of 1 to 6 carbon atoms or aminoalkyl of 1 to 6 carbon atoms, provided that $R^{VII}$ and $R^{VIII}$ may not both by aminoalkyl;

$R_1$ and $R_2$ are independently hydrogen, hydroxy, lower alkyl having 1 to 6 carbon atoms, or lower alkoxy having 1 to 6 carbon atoms;

$R_3$ and $R_4$ are independently hydrogen or lower alkyl having 1 to 6 carbon atoms and each $R_3$ and $R_4$ is independently selected in each —O—CHR$_3$—CHR$_4$— unit;

$R_5$ is hydrogen, alkyl having 1 to 100 carbon atoms, phenyl, aralkyl having 7 to 100 carbon atoms, alkaryl having 7 to 100 carbon atoms, or an acyl group having the formula:

wherein $R_6$ is alkyl having 1 to 30 carbon atoms, phenyl, aralkyl having 7 to 36 carbon atoms or alkaryl having 7 to 36 carbon atoms;

n is an integer from 5 to 100; and x is an integer from 0 to 10.

15. The fuel composition according to claim 14, wherein n is an integer ranging from 8 to 50.

16. The fuel composition according to claim 15, wherein n is an integer ranging from 10 to 30.

17. The fuel composition according to claim 15, wherein $R_1$ is hydrogen, hydroxy, or lower alkyl having 1 to 4 carbon atoms; and $R_2$ is hydrogen.

18. The fuel composition according to claim 17, wherein $R_5$ is hydrogen, alkyl having 1 to 30 carbon atoms, or alkylphenyl having an alkyl group containing 1 to 30 carbon atoms.

19. The fuel composition according to claim 18, wherein $R_1$ is hydrogen or hydroxy.

20. The fuel composition according to claim 19, wherein $A_1$ is selected from the group consisting of $SR^I$, $SO_2R^{III}$, CN, $CO_2R^{VI}$ and $C(O)NR^{VII}R^{VIII}$.

21. The fuel composition according to claim 20, wherein $R_5$ is hydrogen, alkyl having 2 to 24 carbon atoms, or alkylphenyl having an alkyl group containing 2 to 24 carbon atoms.

22. The fuel composition according to claim 21, wherein one of $R_3$ and $R_4$ is lower alkyl having 1 to 3 carbon atoms and the other is hydrogen.

23. The fuel composition according to claim 22, wherein one of $R_3$ and $R_4$ is methyl or ethyl and the other is hydrogen.

24. The fuel composition according to claim 23, wherein x is 0, 1 or 2.

25. The fuel composition according to claim 24, wherein $R_1$ is hydrogen, $R_5$ is alkylphenyl having an alkyl group containing 4 to 12 carbon atoms, and x is 0.

26. The fuel composition according to claim 25, wherein $A_1$ is $SR^I$, $SO_2R^{III}$ or CN.

27. The fuel composition according to claim 14, wherein said composition contains about 50 to about 2500 parts per million by weight of said compound.

28. The fuel composition according to claim 27, wherein said composition further contains about 100 to about 5000 parts per million by weight of a fuel soluble, non-volatile carrier fluid.

29. A fuel concentrate comprising an inert stable oleophilic organic solvent boiling in the range of from about 150° F. to 400° F. and from about 10 to about 70 weight percent of a compound of the formula:

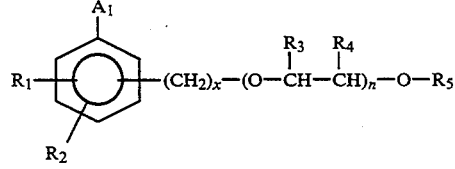

wherein $A_1$ is selected from the group consisting of $SR^I$, $SOR^{II}$, $SO_2R^{III}$, wherein $R^I$, $R^{II}$ and $R^{III}$ are independently lower alkyl of 1 to 6 carbon atoms; $SO_3H$; $SO_2NR^{IV}R^V$, wherein $R^{IV}$ and $R^V$ are independently hydrogen, lower alkyl of 1 to 6 carbon atoms, or aminoalkyl of 1 to 6 carbon atoms, provided that $R^{IV}$ and $R^V$ may not both be aminoalkyl; CN; $CO_2R^{VI}$, wherein $R^{VI}$ is hydrogen or lower alkyl of 1 to 6 carbon atoms; and $C(O)NR^{VII}R^{VIII}$, wherein $R^{VII}$ and $R^{VIII}$ are independently hydrogen, lower alkyl of 1 to 6 carbon atoms or aminoalkyl of 1 to 6 carbon atoms, provided that $R^{VII}$ and $R^{VIII}$ may not both by aminoalkyl;

$R_1$ and $R_2$ are independently hydrogen, hydroxy, lower alkyl having 1 to 6 carbon atoms, or lower alkoxy having 1 to 6 carbon atoms;

$R_3$ and $R_4$ are independently hydrogen or lower alkyl having 1 to 6 carbon atoms and each $R_3$ and $R_4$ is independently selected in each —O—$CHR_3$—$CHR_4$— unit;

$R_5$ is hydrogen, alkyl having 1 to 100 carbon atoms, phenyl, aralkyl having 7 to 100 carbon atoms, alkaryl having 7 to 100 carbon atoms, or an acyl group having the formula:

wherein $R_6$ is alkyl having 1 to 30 carbon atoms, phenyl, aralkyl having 7 to 36 carbon atoms or alkaryl having 7 to 36 carbon atoms;

n is an integer from 5 to 100; and x is an integer from 0 to 10.

30. The fuel concentrate according to claim 29, wherein n is an integer ranging from 8 to 50.

31. The fuel concentrate according to claim 30, wherein n is an integer ranging from 10 to 30.

32. The fuel concentrate according to claim 30, wherein $R_1$ is hydrogen, hydroxy or lower alkyl having 1 to 4 carbon atoms; and $R_2$ is hydrogen.

33. The fuel concentrate according to claim 32, wherein $R_5$ is hydrogen, alkyl having 1 to 30 carbon atoms, or alkylphenyl having an alkyl group containing 1 to 30 carbon atoms.

34. The fuel concentrate according to claim 33, wherein $R_1$ is hydrogen or hydroxy.

35. The fuel concentrate according to claim 34, wherein $A_1$ is selected from the group consisting of $SR^I$, $SO_2R^{III}$, CN, $CO_2R^{VI}$ and $C(O)NR^{VII}R^{VIII}$.

36. The fuel concentrate according to claim 35, wherein $R_5$ is alkyl having 2 to 24 carbon atoms, or alkylphenyl having an alkyl group containing 2 to 24 carbon atoms.

37. The fuel concentrate according to claim 36, wherein one of $R_3$ and $R_4$ is lower alkyl having 1 to 3 carbon atoms and the other is hydrogen.

38. The fuel concentrate according to claim 37, wherein one of $R_3$ and $R_4$ is methyl or ethyl and the other is hydrogen.

39. The fuel concentrate according to claim 38, wherein x is 0, 1 or 2.

40. The fuel concentrate according to claim 39, wherein $R_1$ is hydrogen, $R_5$ is alkylphenyl having an alkyl group containing 4 to 12 carbon atoms, and x is 0.

41. The fuel concentrate according to claim 40, wherein $A_1$ is $SR^I$, $SO_2R^{III}$ or CN.

* * * * *